US012734523B2

(12) United States Patent
Kim et al.

(10) Patent No.: US 12,734,523 B2
(45) Date of Patent: Sep. 15, 2026

(54) THERMAL CYCLER COMPRISING SAMPLE HOLDER ASSEMBLY

(71) Applicant: SEEGENE, INC., Seoul (KR)

(72) Inventors: Young Wook Kim, Seoul (KR); Dong Woo Kang, Seoul (KR); Hye Jin Lee, Anyang-si (KR)

(73) Assignee: Seegene, Inc., Seoul (KR)

( * ) Notice: Subject to any disclaimer, the term of this patent is extended or adjusted under 35 U.S.C. 154(b) by 1208 days.

(21) Appl. No.: 17/439,881

(22) PCT Filed: Mar. 18, 2020

(86) PCT No.: PCT/KR2020/003726
§ 371 (c)(1),
(2) Date: Sep. 16, 2021

(87) PCT Pub. No.: WO2020/190035
PCT Pub. Date: Sep. 24, 2020

(65) Prior Publication Data

US 2022/0184612 A1 Jun. 16, 2022

(30) Foreign Application Priority Data

Mar. 18, 2019 (KR) ........................ 10-2019-0030258

(51) Int. Cl.
*B01L 3/00* (2006.01)
*C12Q 1/686* (2018.01)

(52) U.S. Cl.
CPC ... *B01L 3/50851* (2013.01); *B01L 2300/0609* (2013.01); *B01L 2300/1805* (2013.01); *B01L 2300/1883* (2013.01); *B01L 2300/1894* (2013.01); *C12Q 1/686* (2013.01)

(58) Field of Classification Search
None
See application file for complete search history.

(56) References Cited

U.S. PATENT DOCUMENTS 6,341,490 B1* 1/2002 Jones .................. B01L 3/50851 62/3.2
2004/0065655 A1* 4/2004 Brown ................ B01L 3/50853 219/385
2004/0149725 A1 8/2004 Brown
2005/0006372 A1* 1/2005 Murakami ............ B01L 3/5027 219/385

(Continued)

FOREIGN PATENT DOCUMENTS

JP H10247711 A 9/1998
KR 20020038765 A 5/2002

(Continued)

OTHER PUBLICATIONS

International Search Report and Written Opinion of the ISA issued in PCT/KR2020/003726, mailed Jun. 25, 2020; ISA/KR.

*Primary Examiner* — Brian R Gordon
(74) *Attorney, Agent, or Firm* — Knobbe, Martens, Olson & Bear, LLP

(57) ABSTRACT

Provided a thermal cycler. In a case in which plurality of heat sinks participate in thermal control of a plurality of thermally independent sample holders for reliable nucleic acid reactions of the plurality of sample holder, a barrier is present between the adjacent heat sinks.

4 Claims, 8 Drawing Sheets

(56) References Cited

U.S. PATENT DOCUMENTS

2008/0003649 A1* 1/2008 Maltezos ............ B01L 3/50851 435/286.1
2008/0254517 A1* 10/2008 Mortillaro ................. B01L 7/52 435/283.1
2008/0274511 A1 11/2008 Tan et al.
2009/0011495 A1* 1/2009 Steinmann .......... B01L 3/50851 435/303.1
2009/0139311 A1 6/2009 Lehto et al.
2010/0303690 A1* 12/2010 Howell ..................... B01L 7/52 422/600
2013/0078712 A1 3/2013 Sano et al.
2013/0210127 A1* 8/2013 Williams ................. C12Q 1/68 435/287.2
2013/0240181 A1* 9/2013 Yasunaga ................ F28D 15/00 165/104.28
2014/0038192 A1 2/2014 Buse et al.
2015/0079667 A1* 3/2015 Brahmasandra ......... H05K 3/30 29/611
2015/0238968 A1 8/2015 TerMaat et al.
2016/0144366 A1* 5/2016 Sugiyama ................. B01L 7/52 435/287.2
2016/0339437 A1 11/2016 Evans et al.
2016/0354784 A1* 12/2016 Habrich .................... B01L 7/00
2017/0239663 A1 8/2017 Ceremony et al.
2018/0056296 A1 3/2018 Shin et al.
2019/0383845 A1* 12/2019 Miyazaki ............... G01N 35/04
2020/0209271 A1 7/2020 Lee et al.
2020/0371071 A1* 11/2020 Wada ....................... G01N 1/28

FOREIGN PATENT DOCUMENTS

KR 200285745 Y1 8/2002
KR 10-2012-0111100 A 10/2012
KR 10-2013-0071645 A 7/2013

* cited by examiner

[Figure 6]

[Figure 9]
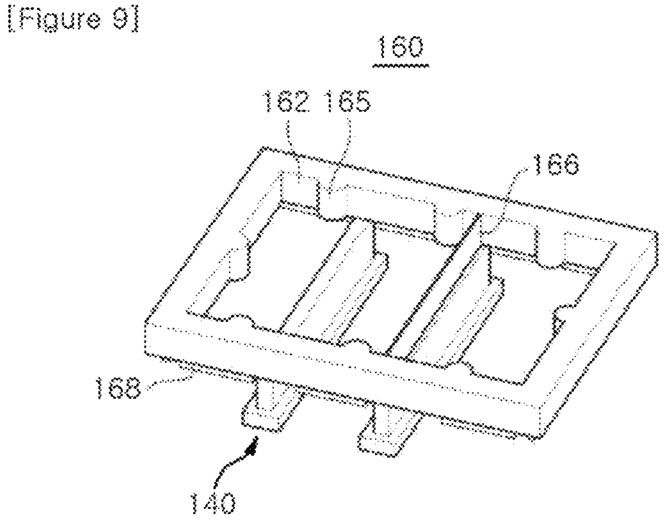

THERMAL CYCLER COMPRISING SAMPLE HOLDER ASSEMBLY

CROSS-REFERENCE TO RELATED APPLICATIONS

This application is a U.S. National Phase Application under 35 U.S.C. 371 of International Application No. PCT/KR2020/003726, filed on Mar. 18, 2020, which claims priority from Korean Patent Application No. 10-2019-0030258, filed on Mar. 18, 2019, in the Korean Intellectual Property Office. The entire disclosures of the above applications are incorporated herein by reference in their entirety.

TECHNICAL FIELD

The present disclosure relates to a thermal cycler for nucleic acid reactions.

BACKGROUND ART

A polynucleotide chain reaction (PCR), most widely used for nucleic acid amplification, includes repeated cycles of denaturation of double-stranded deoxyribonucleic acid (DNA), followed by oligonucleotide primer annealing to a DNA template and primer extension by a DNA polymerase (Mullis, et al., U.S. Pat. Nos. 4,683,195, 4,683,202, and 4,800,159; and Saiki, et al., (1985) Science 230, 1350-1354). The DNA denaturation is performed at about 95° C., and the annealing and primer extension are performed at a temperature lower than 95° C., i.e. a temperature ranging from 55° C. to 75° C.

Thus, a thermal cycler performs nucleic acid amplification reactions on samples accommodated in reaction vessels by repeatedly raising and lowering the temperatures of the reaction vessels included in a sample holder. Here, heat provided to the sample holder is generated by a heat-generating element, and it is necessary to discharge the heat generated by the heat-generating element outwardly through a heat sink.

In general, a thermal cycler cools a heat sink using a cooling fan connected to a motor so that hot air around the heat sink is discharged through a passage.

Such a heat sink may have a configuration corresponding to the heat-generating element to efficiently realize heat dissipation performance.

In a thermal cycler including a plurality of sample holders thermally independent of each other, it is necessary to control the sample holders to be thermally independent of each other. In this regard, a heat-generating element and a heat sink may be provided for each of the sample holders. However, in a plurality of heat sinks provided for a plurality of sample holders, thermal interference in airflows may occur between adjacent heat sinks.

DISCLOSURE OF INVENTION

Technical Problem

Accordingly, the present disclosure proposes a sample holder assembly having a barrier, the sample holder assembly being useful in a thermal cycler for nucleic acid reactions.

Solution to Problem

According to an aspect of the present disclosure, provided is a thermal cycler including a sample holder assembly. The sample holder assembly may include: a plurality of sample holders thermally independent of each other, each of the plurality of sample holders being configured to accommodate a sample or a sample reaction vessel; a plurality of heat-generating elements controlling temperatures of the plurality of sample holders, one or more heat-generating elements among the plurality of heat-generating elements being thermally coupled to each of the plurality of sample holders; and a plurality of heat sinks cooling the plurality of sample holders, one or more heat sinks among the plurality of heat sinks being thermally coupled to each of the plurality of sample holders.

According to embodiments of the present disclosure, the sample holder assembly may further include a plurality of cooling fans cooling the plurality of heat sinks.

According to embodiments of the present disclosure, one or more cooling fans among the plurality of cooling fans may be disposed for each of the plurality of sample holders.

According to embodiments of the present disclosure, the sample holder assembly may further include a barrier preventing thermal interference between adjacent heat sinks among the plurality of heat sinks.

According to embodiments of the present disclosure, the barrier may be located between the adjacent heat sinks thermally coupled to different sample holders among the plurality of sample holders.

According to embodiments of the present disclosure, the barrier may not be located between the adjacent heat sinks thermally coupled to a single sample holder among the plurality of sample holders.

According to embodiments of the present disclosure, the barrier may be located between all of the adjacent heat sinks.

According to embodiments of the present disclosure, the sample holder assembly may further include a barrier separating airflow passages of adjacent cooling fans among the plurality of cooling fans.

According to embodiments of the present disclosure, the barrier may be located between the airflow passages of the adjacent cooling fans disposed on different sample holders among the plurality of sample holders.

According to embodiments of the present disclosure, the barrier may not be located between the airflow passages of the adjacent cooling fans disposed on different sample holders among the plurality of sample holders.

According to embodiments of the present disclosure, the barrier may be located between the airflow passages of all of the adjacent cooling fans.

According to embodiments of the present disclosure, the sample holder assembly may further include a barrier located between adjacent heat sinks, among the plurality of heat sinks thermally, connected to different sample holders among the plurality of sample holders and between airflow passages of adjacent cooling fans , among the plurality of cooling fans , disposed on different sample holders among the plurality of sample holders.

According to embodiments of the present disclosure, the sample holder assembly may further include a barrier located between different sample holders among the plurality of sample holders and/or between adjacent heat-generating elements, among the plurality of heat-generating elements, connected to the different sample holders.

According to embodiments of the present disclosure, the sample holder assembly may have a configuration in which the plurality of sample holders, the plurality of heat-generating elements, and the plurality of heat sinks may be arranged in order in a top to bottom direction. The plurality of cooling fans may be disposed below or on sides of the plurality of heat sinks.

According to embodiments of the present disclosure, the sample holder assembly may further include a sample holder accommodating unit. The sample holder accommodating unit is a frame open through top and bottom portions thereof, and includes a receiving portion configured to accommodate the plurality of sample holders. The barrier may be connected to a bottom portion of the sample holder accommodating unit.

According to embodiments of the present disclosure, the sample holder assembly may be accommodated in a housing of the sample holder assembly, and the barrier may be coupled to the housing.

According to embodiments of the present disclosure, the barrier may include a clamping portion allowing the barrier to be bounded to a portion of the plurality of heat sinks or a portion of a plurality of cooling fans.

Advantageous Effects of Invention

The thermal cycler according to embodiments of the present disclosure uses individual heat sinks and individual cooling fans for the sample holders thermally independent of each other, so that the temperatures of the sample holders may be controlled independently of each other.

In the thermal cycler according to embodiments of the present disclosure, the barrier is present between the adjacent heat sinks, so that heat dissipation may be efficiently performed without an interference in air currents between the adjacent heat sinks.

In the thermal cycler according to embodiments of the present disclosure, the barrier is present between airflow passages of the adjacent cooling fans, so that an individual cooling fan may cool the corresponding heat sink without being affected by another cooling fan.

BRIEF DESCRIPTION OF DRAWINGS

FIG. 9 is a perspective view illustrating sample holder accommodating unit according to an implementation of the present disclosure, in which three sample holders are accommodated.

MODE FOR THE INVENTION

Figure 1A:
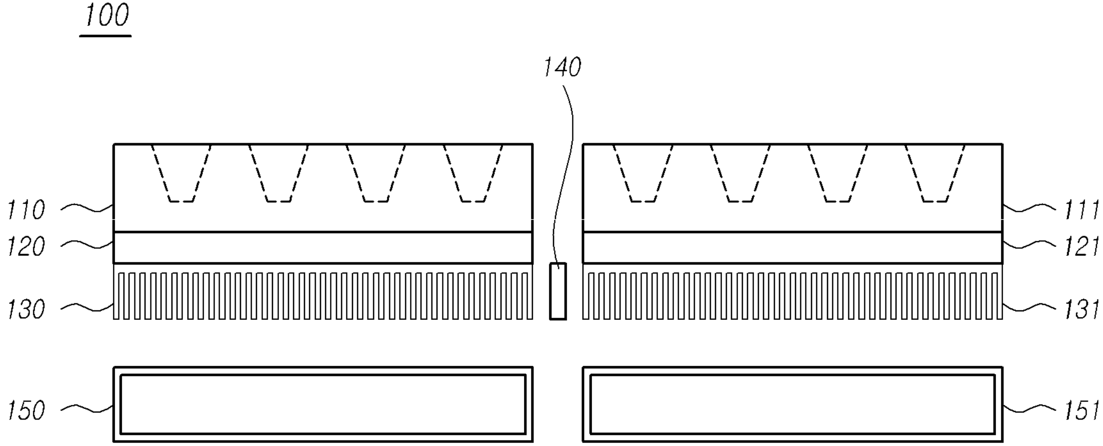
FIGS. 1A to 1C are side views illustrating a sample holder assembly according to embodiments of the present disclosure.

Hereinafter, the present disclosure will be described in detail with reference to the accompanying drawings.

In designating elements of the drawings by reference numerals, the same elements will be designated by the same reference numerals although they are shown in different drawings. Further, in the following description of the present disclosure, a detailed description of known functions and configurations incorporated herein will be omitted in the situation in which the subject matter of the present disclosure may be rendered rather unclear thereby.

In addition, terms, such as first, second, A, B, (a), (b) or the like may be used herein when describing components of the present disclosure. Each of these terminologies is not used to define an essence, order or sequence of a corresponding component but used merely to distinguish the corresponding component from other component(s). In the case that it is described that a certain structural element "is connected to", "is coupled to", or "is in contact with" another structural element, it should be interpreted that another structural element may "be connected to", "be coupled to", or "be in contact with" the structural elements as well as that the certain structural element is directly connected to or is in direct contact with another structural element.

Hereinafter, embodiments of the present disclosure will be described in detail with reference to the accompanying illustrative drawings so that a person having ordinary skill in the art to which the present disclosure relates could easily put the present disclosure into practice.

A variety of nucleic acid amplification reactions may be performed using a thermal cycler according to the present disclosure. For example, such a nucleic acid amplification reaction may be performed by polymerase chain reaction (PCR), ligase chain reaction (LCR; see Wiedmann M, et al., "Ligase chain reaction (LCR)-overview and applications," PCR Methods and Applications 1994 Feb; 3(4): S51-64), gap filling LCR (GLCR; see WO 90/01069, European Patent No. 439182, and WO 93/00447), Q-beta replicase amplification (Q-beta; see Cahill P, et al., Clin Chem., 37(9): 1482-5(1991), U.S. Pat. No. 5,556,751), strand displacement amplification (SDA; see G T Walker, et al., Nucleic Acids Res. 20(7): 16911696(1992), European Patent No. 497272), nucleic acid sequence-based amplification (NASBA; see Compton, J. Nature 350(6313): 912(1991)), transcription-mediated amplification (TMA; see Hofmann WP, et al., J Clin Virol. 32(4): 289-93(2005); U.S. Pat. No. 5,888,779), rolling circle amplification (RCA; see Hutchison C. A., et al., Proc. Natl Acad. Sci. USA. 102: 1733217336 (2005)), or the like.

In particular, the thermal cycler according to the present disclosure is useful for nucleic acid amplification reactions based on polymerase chain reactions. A variety of nucleic acid amplification methods based on polymerase chain reactions have been known in the art. For example, such nucleic acid amplification methods include quantitative PCR, digital PCR, asymmetric PCR, reverse transcriptase PCR (RT-PCR), differential display PCR (DD-PCR), nested PCR, arbitrary priming PCR (AP-PCR), multiplex PCR, SNP genotyping PCR, and the like.

In a case in which a predetermined reaction is repeated or the repetition of a reaction occurs for a predetermine time interval, the term "cycle" as used herein refers to a single repeating unit.

For example, in the PCR, a single cycle refers to a reaction including heat denaturation of a nucleic acid, hybridization or annealing of the nucleic acid with a primer, and primer extension. In this case, a change in predetermined conditions is an increase in the number of repetitions, and the repeating unit in reactions, including a series of the above-described operations, is set to be a single cycle.

The thermal cycler according to the present disclosure (not shown) includes a sample holder assembly 100. The sample holder assembly 100 is located in a predetermined space within the thermal cycler.

Figure 1B:
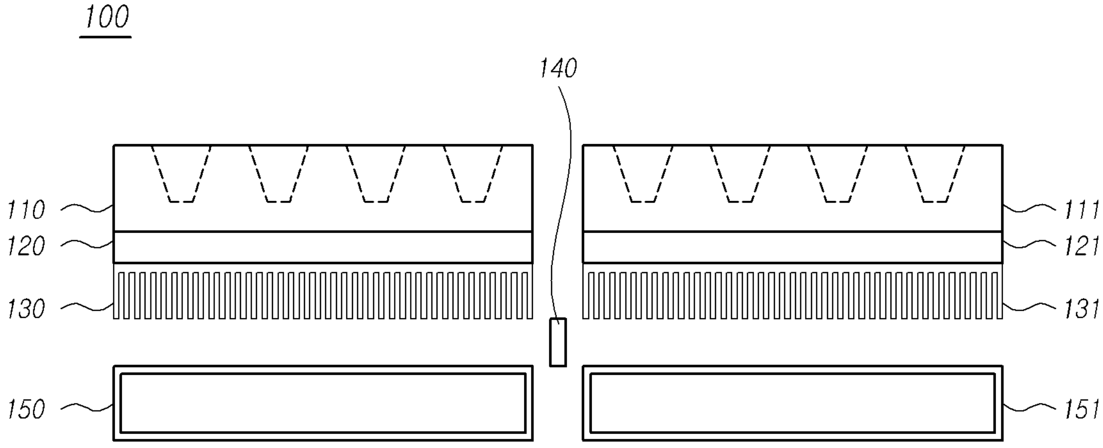
Figure 1C:
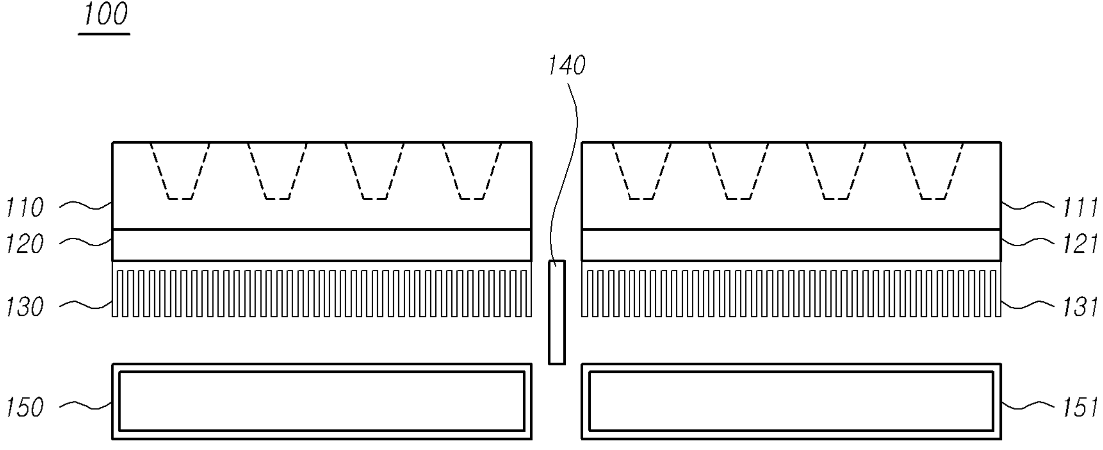

FIGS. 1A to 1C are side views illustrating a variety of implementations of the sample holder assembly 100 according to the present disclosure.

Referring to FIGS. 1A to 1C, the sample holder assembly 100 includes a plurality of sample holders 110 and 111, a plurality of heat-generating elements 120 and 121, and a plurality of heat sinks 130 and 131.

According to another implementation, the sample holder assembly 100 includes the plurality of sample holders 110 and 111, the plurality of heat-generating elements 120 and 121, the plurality of heat sinks 130 and 131, and cooling fans 150 and 151.

According to another implementation, the sample holder assembly 100 includes the plurality of sample holders 110 and 111, the plurality of heat-generating elements 120 and 121, the plurality of heat sinks 130 and 131, the cooling fans 150 and 151, and a barrier 140.

The term used herein "sample" refers to any cell, tissue, or fluid from a biological source, or any other medium that can advantageously be evaluated according to this invention, including virus, bacteria, tissue, cell, blood, serum, plasma, lymph, sputum, swab, aspirate, bronchoalveolar lavage fluid, milk, urine, faeces, ocular fluid, saliva, semen, brain extracts, spinal cord fluid (SCF), appendix, spleen and tonsillar tissue extracts, amniotic fluid, ascitic fluid and non-biological samples {e.g., food and water). The sample also includes solution or solid substance for chemical reaction. In addition, the sample includes natural-occurring nucleic acid molecules isolated from biological sources and synthetic nucleic acid molecules.

The sample holder 110 is a component directly accommodating a sample or accommodating a reaction vessel including a sample.

In an implementation in which the sample holder 110 directly accommodates a sample, the sample holder 110 may be mounted on the device when the device is operated, instead of being fixed to the device.

The expression that "the sample holder 110 may accommodate a sample" as represented herein may be used to comprehensively refer to a case in which the sample holder 110 directly accommodates a sample or a case in which the sample holder 110 accommodates a reaction vessel including a sample.

The heat-generating element 120 may supply heat to the sample holder 110, so that the heat is transferred to the sample directly accommodated in the sample holder 110 or the sample accommodated in the reaction vessel.

The sample holder 110 accommodating the reaction vessels may have the shape of a block or a plate. The sample holder 110 accommodating the reaction vessels may include recesses (e.g. wells) to accommodate the reaction vessels or may have a flat surface. The sample holder 110 accommodating the reaction vessels may have a structure by which the positions of the reaction vessels may be guided or the reaction vessels may be fixed.

A single sample holder 110 is fabricated such that the single sample holder 110 may accommodate one or more samples.

A typical example of the sample holder 110 accommodating the reaction vessels is a thermal block. the thermal block may include a plurality of wells or holes respectively allowing a reaction vessel to be accommodated therein.

The sample holder 110 accommodating the reaction vessels may refer to a state in which the reaction vessels are disposed in the plurality of wells of the sample holder 110 or are disposed on assigned positions of the sample holder.

The reaction vessels are respectively used to accommodate a sample to be analyzed.

Examples of the reaction vessel include a variety of shapes, e.g. a tube, a vial, a strip to which a plurality of single tubes are connected, a plate to which a plurality of tubes are connected, a microcard, a chip, a cuvette, or a cartridge.

The reaction vessel may be made of a variety of materials, such as plastic, ceramic, glass, or metal.

The sample holder 110 directly accommodating the samples may have the above-described shapes of the reaction vessel. The sample holder 110 directly accommodating the samples may be made of the above-described materials of the reaction vessel.

In an implementation, the sample holder 110 is made of a thermally conductive material. When the sample holder 110 is in direct contact with the samples or in contact with the reaction vessels, heat may be transferred from the sample holder 110 to the samples in the sample holder or the samples in the reaction vessels.

The sample holder 110 may be made of a metal, such as aluminum (Al), gold (Au), silver (Ag), nickel (Ni), or copper (Cu), or may be made of plastic or ceramic.

In an implementation in which the sample holder 110 is a block, hollow spaces may be provided between the wells to reduce heat capacity.

In an implementation, the plurality of wells of the sample holder 110 are regularly arranged. For example, the plurality of wells are arranged in a matrix consisting of columns and rows. The plurality of wells may be provided as, for example, 16 wells having a 4×4 array, 24 wells having a 6×4 array, 32 wells having a 4×8 array, 60 wells having a 5×12 array, 90 wells having a 5×18 array, and 96 wells having an 8×12 array. The 16 wells, the 32 wells, and the 96 wells may generally be used, although the present disclosure is not limited thereto.

The shape, size, or the like of the wells may be determined to be adequate to the reaction vessels accommodated therein.

In an implementation, the number of the wells of the sample holder 110 is equal to or less than 500, 400, 300, 200, 100, or 50.

In an implementation, the number of the wells of the sample holder 110 is equal to or more than 4, 8, 10, 20, 30, or 40.

In the sample holder assembly 100 according to the present disclosure, the sample holders 110 as described above are provided in plural. Each of the sample holders 110 and 111 are thermally independent of each other.

The thermally independent sample holders 110 and 111 refer to sample holders with no heat exchange occurring therebetween. In an implementation, the thermally independent sample holders 110 and 111 may be spaced apart from each other instead of being adjacent, with an insulator or a hollow space being present therebetween.

In an implementation, a single reaction vessel (e.g. a 96 micro-well pate) may be mounted on the plurality of thermally independent sample holders (or thermal blocks). The reaction vessel made of a material having no or insignificant heat exchange between the wells disposed in different thermal blocks is used.

The sample holder 110 is thermally coupled to the heat-generating element 120, and the temperature of the sample holder 110 may be increased using heat provided by the heat-generating element 120.

The heat-generating element 120 may have a variety of shapes depending on implementations of the sample holder 110 or methods of supplying electricity to the sample holder 110. For example, the heat-generating element 120 may have the shape of a polygonal plate having an area capable of covering a specific area of the sample holder 110 or the shape of a hot wire produced by compressing an electrically conductive terminal into the shape of a line. Such heat-generating elements 120 and 121 may be electrically connected to a power module to generate heat using power supplied by the power module.

In an implementation, the heat-generating element 120 may be controlled by a controller. In an implementation, the heat-generating element 120 is a thermoelectric module. For example, the heat-generating element 120 is a Peltier element. In an implementation, the thermoelectric module may be provided as a component separate from the sample holder 110. In an implementation, the thermoelectric module is located below the sample holder 110.

In another implementation, the heat-generating element 120 is a resistance heating element. For example, the resistance heating element is made of metal, ceramic, or a semiconductor, and may have a structure comprised of one or more strands or the shape of a plate, a foil, a film, or the like.

In an implementation, the resistance heating element may be connected to the sample holder 110 in a manner in which the resistance heating element is detachably attached to the sample holder 110 or in an inseparable manner. In an implementation, the resistance heating element may be located below the sample holder 110. In an implementation, the resistance heating element may be connected to the sample holder 110 while surrounding at least a portion of a space in which the samples are accommodated.

Depending on the heat-generating element 120 used, the heat-generating element 120 may not only heat the sample holder 110 but may also cool the sample holder 110. For example, a Peltier element may heat and cool the sample holder 110.

The term "thermally coupled" used in relation to the sample holder 110 and the heat-generating element 120 refers to a situation in which the heat-generating element 120 is directly or indirectly connected to or in contact with the sample holder 110, such that the heat-generating element 120 may exchange heat with or transfer or conduct heat to the sample holder 110.

For example, not only a situation in which the sample holder 110 is in direct contact with the heat-generating element 120 but also a situation in which a heat conducting component (e.g. a heat conducting plate, foil, film, or grease) is present between the sample holder 110 and the heat-generating element 120 may be represented as being thermally coupled.

The term "disposition of the heat-generating element 120" used in relation to the sample holders 110 and 111 and the heat-generating elements refers to the heat-generating element 120 being disposed in a position in which the heat-generating element 120 may control the temperature of sample holder 110. The term may refer to a situation in which the sample holder 110 and the heat-generating element 110 controlling the temperature of the sample holder 110 are in a thermally coupled state.

The heat-generating element 120 may be disposed on a side surface of or below the sample holders 110 and 111. In particular, the heat-generating element 120 may be disposed to be adjacent to and in contact with the sample holders 110 and 111.

The plurality of thermally independent sample holders 110 and 111 may be temperature-controlled by the heat-generating elements 120 and 121 assigned thereto respectively.

The heat-generating element 120, thermally coupled to the sample holder 110, is required to not be thermally coupled to the other sample holder 111 thermally independent of the sample holder 110.

The heat-generating element 120 may be controlled respectively (or independently) to respectively control the temperature of the sample holder 110.

In an implementation, one or more heat-generating elements 120 are disposed on the sample holder 110, and the sample holder 110 is thermally coupled to the heat-generating elements 120.

Figure 2:
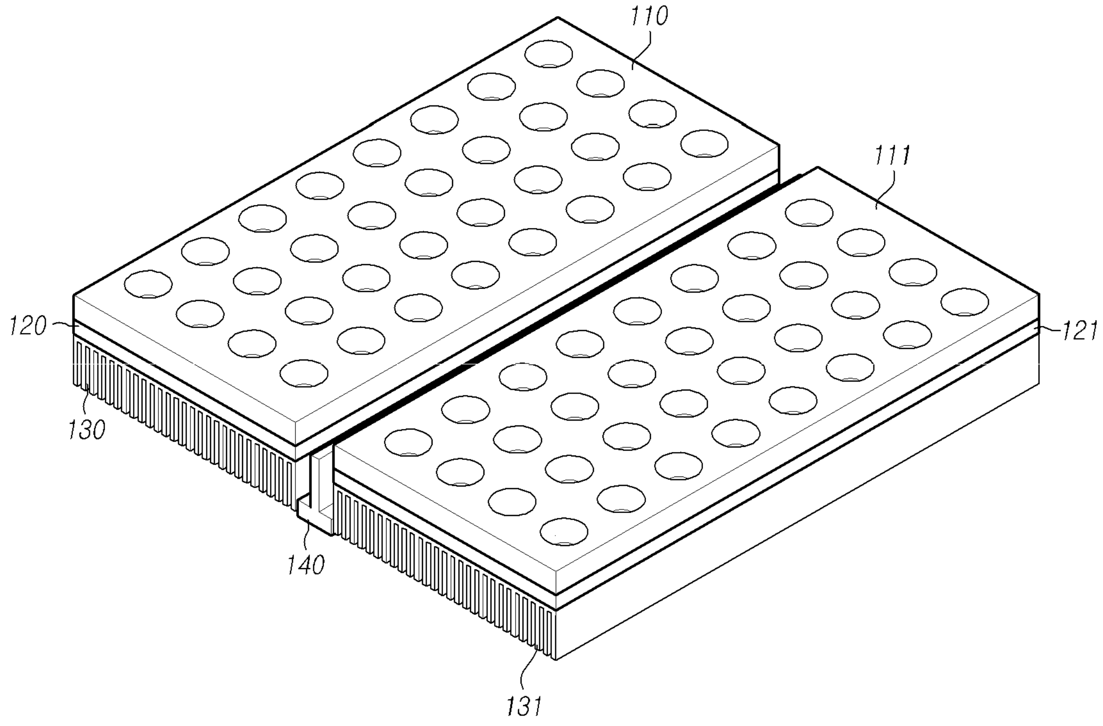
FIGS. 2 to 4 are perspective views illustrating the sample holder assembly according to embodiments of the present disclosure.

In an implementation, as illustrated in FIG. 2, a single heat-generating element 120 or 121 having an area capable of sufficiently covering the bottom side of a single sample holder 110 or 111 may be disposed below the single sample holder 110 or 111.

Figure 3:
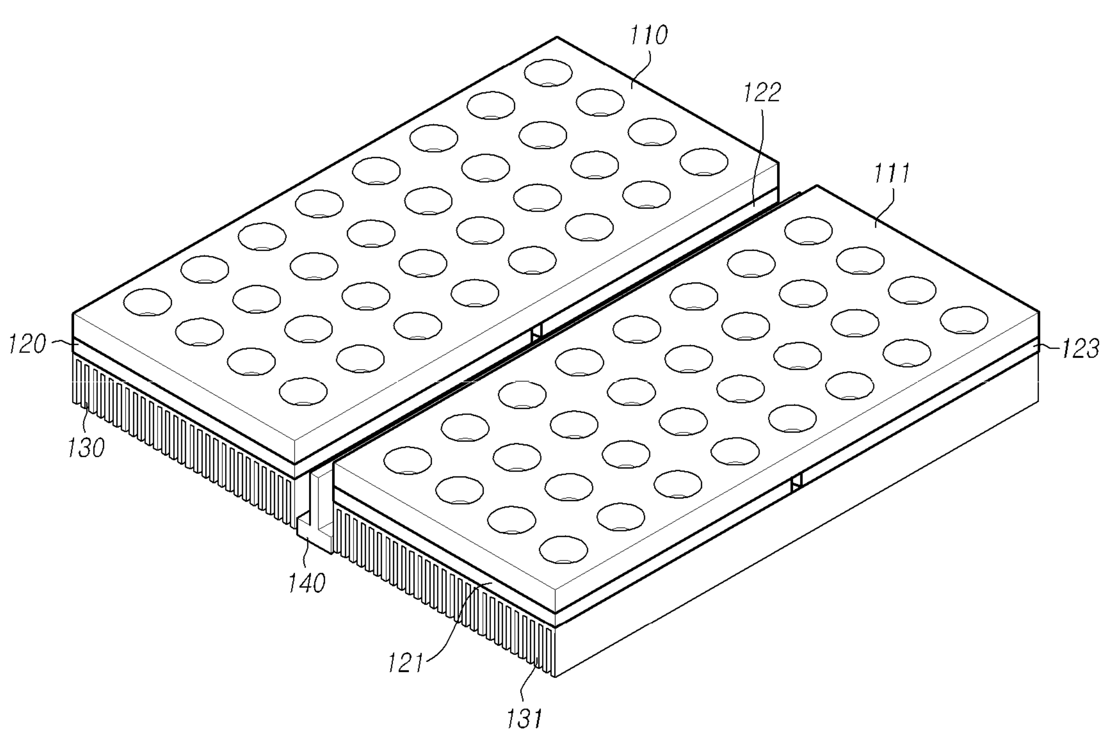

In an implementation, as illustrated in FIG. 3, two heat-generating elements 121 and 123 may be disposed below a single sample holder 111.

For example, in a case in which the sample holder 111 is a sample holder having the 32 well structure, two heat-generating elements 121 and 123 respectively having an area capable of covering 16 wells may be provided.

In an implementation, one or more thermally coupled heat-generating elements 120 may be used to control the temperature of the single thermally independent sample holder. In particular, 1, 2, 3, or 4 heat-generating elements 120 may be used. In a case in which the plurality of heat-generating elements 120 are used for the single sample holder 110, each of the plurality of heat-generating elements 120 may be controlled independently or the entirety of the plurality of heat-generating elements 120 may be controlled in the manner of a single heat-generating element 120.

In an implementation, a thermally conductive material layer may be present between the sample holder 110 and the heat-generating element 120. For example, the thermally conductive material includes metal, ceramic, graphite, grease, an adhesive, and the like. The thermally conductive material may serve to improve heat dispersion, heat conductivity, or the like or improve adhesion between the sample holder 110 and the heat-generating element 120.

The sample holder assembly 100 according to the present disclosure is characterized in that an individual heat sink 130 is assigned to each of the plurality of thermally independent sample holders 110. This allows the temperatures of the plurality of sample holders 110 to be controlled more independently.

The heat sink 130 is a component used as a passive heat exchanger to efficiently dissipate heat from the sample holder 110.

The term "thermally coupled" used in relation to the sample holder 110 and the heat sink 130 refers to a situation in which the heat sink 130 is directly or indirectly connected to or in contact with the sample holder 110, such that the heat sink 130 may exchange heat with or transfer or conduct heat from or to the sample holder 110.

For example, not only a situation in which the sample holder 110 is in direct contact with the heat sink 130 but also a situation in which the heat-generating element 120 is present between the sample holder 110 and the heat sink 130, the sample holder 110 and the heat sink 130 may be referred to as being thermally coupled. For example, in such a situation, a Peltier element or a plate or film-shaped resistance heating element is present.

In an implementation in which the heat-generating element 120 is implemented as a resistance heating element comprised of a wire, the sample holder 110 and the heat sink 130 may be in direct contact with each other.

In addition, a situation in which the heat conducting components (e.g. a heat conducting plate, foil, film, or grease) is present between the sample holder 110 and the heat sink 130 may be represented as being thermally coupled.

In addition, a situation in which the heat-generating element 120, a Peltier element, is present between the sample holder 110 and the heat sink 130 and the heat conducting components are present between the heat-generating element 120 and the sample holder 110 and between the heat-generating element 120 and the heat sink 130, respectively, may be represented as being thermally coupled.

The heat sink 130 may be thermally coupled to the heat-generating element 120. In this case, the heat sink 130 may be a component used to dissipate heat from the heat-generating element 120.

The term "thermally coupled" used in relation to the heat sink 130 and the heat-generating element 120 refers to a situation in which the heat sink 130 is directly or indirectly connected to or in contact with the heat-generating element 120, such that the heat sink 130 may exchange heat with or transfer or conduct heat from the heat-generating element 120.

The term "disposition of the heat sink 130" used in relation to the sample holder 110 or the heat-generating element 120 refers to the heat sink 130 being disposed in a position in which the heat sink 130 may sufficiently dissipate heat from the sample holder 110 or the heat-generating element 120. The term may refer to a situation in which the heat sink 130 dissipating heat from the sample holder 110 or the heat-generating element 120 is thermally coupled to the same component.

The heat sink 130, thermally coupled to the sample holder 110, is required to not be thermally coupled to the other sample holder 111 thermally independent of the sample holder 110. The heat sink 130, used to cool the heat-generating element 120 thermally coupled to the sample holder 110, is not used to cool the heat-generating element 120 thermally coupled to the other sample holder 111 thermally independent of the sample holder 110.

In an implementation, the heat sink 130 may be located below the sample holder 110 or the heat-generating element 120. In particular, the heat sink 130 may be disposed to be adjacent to and in contact with the heat-generating element 120.

In an implementation, the heat sink 130 may be located on a side surface of the sample holder 110 or the heat-generating element 120. In this case, a heat pipe may be used as a medium.

The heat sink 130 may be made of metal, ceramic, or plastic. The heat sink 130 may include a plurality of heat dissipation fins to increase a heat dissipation area. The heat sink 130 may use fins having a variety of shapes. For example, the fin types of the heat sink include a pin fin, a straight fin, or a flared fin.

The plurality of heat dissipation fins may be aligned vertically on a base of the heat sink or may be radially arranged. The heat dissipation fins provided on the heat sink 130 may be arranged in a variety of directions depending on embodiments. For example, straight fins may be arranged in the X-axis direction or the Y-axis direction of the base of the heat sink 130.

In an implementation, the straight fins cut at predetermined distances may be arranged. The shape, number, height, width, and length of the heat dissipation fins used may be selectively adjusted to optimize heat dissipation performance of the heat sink.

The direction in which the heat dissipation fins are arranged on the heat sink may serve as a direction in which air is discharged.

The thermal cycler according to the present disclosure may include air circulation passages in opposite side portions, the bottom portion, and the rear portion.

The thermal cycler according to the present disclosure may use a variety of heat sinks known in the art.

The plurality of sample holders 110 thermally independent of each other may be cooled by the heat sinks 130 assigned thereto respectively.

In an implementation, the plurality of sample holders 110 and 111 thermally independent of each other are not thermally coupled to a single heat sink 130.

In an implementation, one or more heat sinks 130 are disposed on each of the sample holders 110. The sample holders 110 are thermally coupled to the heat sinks 130.

In an implementation, one or more heat sinks 130 are disposed on each of the heat-generating elements 120. The heat-generating elements 120 are thermally coupled to the heat sinks 130.

In an implementation, as illustrated in FIG. 2, a single heat sink 131 having an area capable of sufficiently covering the bottom side of a single heat-generating element 121 may be disposed below the single heat-generating element 121.

Figure 4:
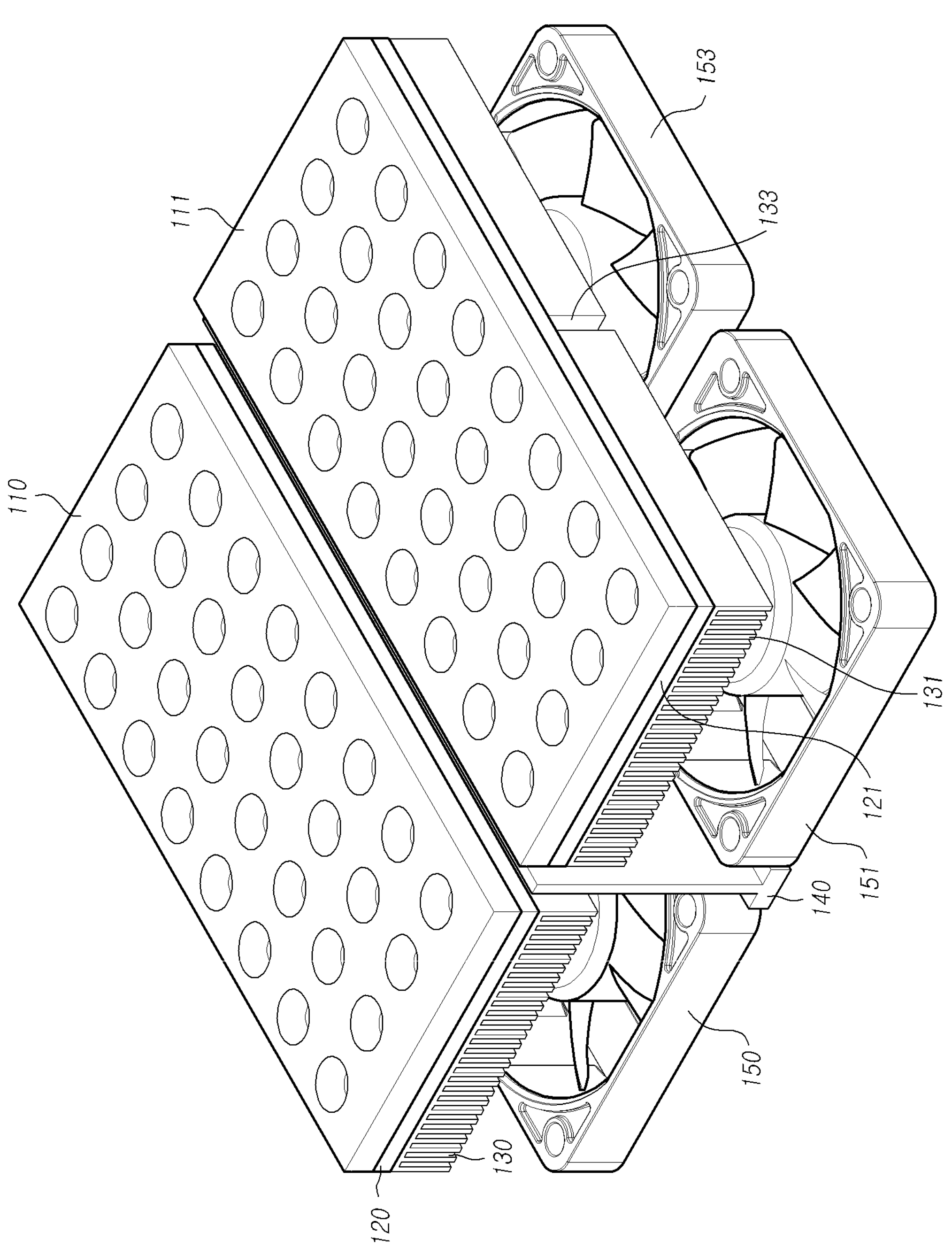

In another implementation, as illustrated in FIG. 4, two heat sinks 131 and 133 may be disposed below a single heat-generating element 121. For example, in a case in which the heat-generating element 121 covers the sample holder 111 having the 32 well structure, the heat sinks 131 and 133 may be provided as two heat sinks 131 and 133 respectively having an area capable of covering 16 wells may be provided.

In an implementation, in some heat-generating elements 121 and 123, a single heat sink 131 may be disposed on the heat-generating elements 121 and 123. As illustrated in FIG. 3, in a case in which two or more heat-generating elements 121 and 123 are disposed on a single sample holder 111, a single heat sink 131 may be disposed on the heat-generating elements 121 and 123. In this implementation, since the plurality of heat-generating elements 121 and 123 are used to control the temperature of the common sample holder 111, an individual heat sink 131 may not be used for each of the heat-generating elements 121 and 123.

In an implementation, one or more heat sink 130 thermally coupled to each other may be used for a single thermally independent sample holder 110. In particular, 1, 2, 3, or 4 heat sinks 130 may be used.

The sample holder assembly 100 according to the present disclosure further includes the cooling fan 150.

The sample holder assembly according to the present disclosure is characterized in that the cooling fans 150 and 151 are disposed on the plurality of thermally independent sample holders 110 and 111, respectively.

The heat sinks 130 and 131 are provided for the plurality of thermally independent sample holders 110 and 111, respectively. The cooling fans 150 and 151 may be provided for the heat sinks 130 and 131, respectively.

The respectively disposed cooling fans 150 and 151 may be on/off controlled, so that the plurality of sample holders 110 and 111 may be temperature-controlled independently of each other.

The term "disposition the heat sink 130" used in relation to the sample holder 110 and the cooling fan 150 refers to the cooling fan 150 being disposed in a position in which the heat sink 130 may dissipate heat from the sample holder 110. The cooling fan 150 may cool the sample holder 110 by cooling the heat sink 130 thermally coupled to the sample holder 110, instead of directly cooling the sample holder 110. This term may also refer to the cooling fan 130 being disposed in a position in which heat may be dissipated from the cooling fan 130 thermally coupled to the sample holder 110.

The cooling fan 150 used (or disposed) to cool the sample holder 110 is not used (or disposed) to cool the other sample holder 111 thermally independent of the sample holder 110.

The cooling fan 150 used (or disposed) to cool the heat sink 130 thermally coupled to the sample holder 110 is not used (or disposed) to cool the heat sink 131 thermally coupled to the other sample holder 111 thermally independent of the sample holder 110.

In an implementation, the cooling fan 150 generates an airflow in response to the rotation of the motor, thereby cooling the sample holder 110 or the heat sink 130.

The cooling fan 150 may be implemented as various types of cooling fans known in the art. For example, cooling fan 150 may be implemented as an axial fan, a centrifugal fan, or a cross flow fan.

The cooling fan 150 may move air cross the heat sink 130 to cool a component thermally coupled to the heat sink 130. For example, in the sample holder assembly 100 in which the sample holder 110, the heat-generating element 120, and the heat sink 130 are thermally coupled in order, the cooling fan 150 contributes to cooling these components. In particular, the cooling fan 150 contributes to cooling the sample holder 110.

The plurality of cooling fan 150 used in the device according to the present disclosure may be controlled independently of each other. For example, the plurality of cooling fans 150 may be on/off controlled individually.

In an implementation, when one sample holder 110 is being heated while another sample holder 111 is being cooled, one cooling fan 150 used for the sample holder 110 in the heating process may be stopped, and the cooling fan 151 used for the sample holder 111 in the cooling process may be operated.

One or more cooling fans 150 may be used for the cooling of a single thermally independent sample holder 110. In an implementation, 1, 2, 3, or 4 cooling fans 150 are used for the cooling of a single sample holder. In a case in which a plurality of cooling fans 150 are used for the cooling of a single sample holder 110, each of the plurality of cooling fans 150 may be controlled independently or the entirety of the plurality of cooling fan 150 may be controlled in the manner of a single cooling fan 150.

In a case in which the cooling fan 150 cools the heat sink 130 by generating an airflow, the cooling fan 150 may be located on at least one selected from among the bottom surface, the front surface, the rear surface, the left surface, the right surface, or combinations thereof, of the heat sink 130, to cool the heat sink 130.

In an implementation, the position of the cooling fan 150 is determined in consideration of a direction in which the heat dissipation fins of the heat sink 130 are arranged.

In the situations illustrated in FIGS. 1A to 1C and FIG. 4, the cooling fan 150 is located on the bottom surface of the heat sink 130. In the situation illustrated in FIG. 5, the cooling fan 150 is located on the front surface of the heat sink 130. In particular, in FIG. 5, the cooling fan 150 is located on the front surface of the heat sink 130, in consideration of the direction of the fins arranged from the front surface to the rear surface of the heat sink 130.

In an implementation, the cooling fan 150 is placed within a distance of 1 cm, 2 cm, 3 cm, 5 cm, 10 cm, or 20 cm from the heat sink 130.

In an implementation, the cooling fan 150 is placed at a distance of 0.3 cm to 10 cm from the heat sink 130.

In an implementation, the cooling fan 150 is placed in contact with the heat sink 130.

In an implementation, the sample holder assembly 100 may further include a sealing structure or an airflow guide structure to prevent an airflow generated by the cooling fan 150 from arriving at the sample holder 110 or the heat-generating element 120.

The cooling fan 150 is located at a distance from the heat sink 130, instead of being in direct contact with the heat sink 130.

The sample holder assembly 100 according to the present disclosure includes the barrier 140 for the heat sink and/or the cooling fan.

In FIG. 1A, the barrier 140 is located between the adjacent heat sinks 130 and 131 to prevent interference of air conditions between the heat sinks. The air conditions refer to an airflow, such as an air current or a wind direction, or a temperature of air, induced in the heat sinks 130 and 131 by the cooling fans 150 and 151, respectively.

The thermal cycler according to the present disclosure causes an airflow using the rotation of the cooling fan 150 to cool the heat sink, so that a specific air condition is provided in the heat sink 130. In a case in which the plurality of heat sinks are disposed, air currents may interfere with each other to cause air collision between the heat sinks, in which corresponding surfaces of the heat sinks face each other, so that a specific air condition of each heat sink may be changed.

This phenomenon may affect the heat dissipation performance of the heat sink, thereby resulting in a situation in which the temperatures of the sample holders 110 and 111 are not accurately controlled.

Therefore, according to the present disclosure, the barrier 140 is configured such that hot airflow is discharged in an intended direction in each of the heat sinks 130 and 131 without an thermal interference in the air conditions among the plurality of heat sinks 130 and 131.

In an implementation, the sample holder assembly 100 includes the barrier present between one or more heat sinks 130 and 131 among the adjacent heat sinks.

The barrier 140 may be made of a variety of materials as long as the barrier may block airflows. The barrier 140 may be made of metal, such as Al, acryl, polycarbonate, transparent (or semitransparent) resin, rubber, ceramic, or the like.

In an implementation, the barrier 140 may be made of, in particular, an insulating material that hardly conducts heat.

In an implementation, an area that the barrier 140 blocks may be greater than or equal to one surface that each of the heat sinks 130 and 131 faces.

In an implementation, the barrier 140 having the above-described shape may guide an airflow through the passage defined thereby. The airflow may be guided or directed in a single direction, e.g. a direction in which the passage is located, by the barrier 140.

The barrier 140 according to an implementation of the present disclosure may be configured to block at least a space or area between the heat sinks.

According to an implementation of the present disclosure, the barrier 140 may have the shape of a vertical line, as illustrated in FIG. 1A. In another implementation, as illustrated in FIGS. 2 to 4, the barrier 140 may have an inverted T-shaped configuration, in which the bottom end thereof protrudes outward while the top end thereof does not protrude outward. In another implementation, the barrier 140 may be configured such that only the top end thereof protrudes or both the top end and the bottom end protrude.

The heat sinks 130 and 131 may be located to be adjacently in contact with or at a distance from the barrier 140.

The above-described protruding configuration may block air flowing through above or below the heat sinks 130 and 131.

In the barrier 140 having the above-described configuration, the protruding portion may be provided on the entirety of the top end or the bottom end or may be provided on a portion of the top end or the bottom end.

In addition, according to an implementation of the present disclosure, a seal may be provided on a gap between the barrier 140 and the heat sink 130. This seal may shield the sample holder 110 or the heat-generating element 120 located above the heat sink 130 from hot air of the heat sink 130.

The seal may be implemented by a variety of methods. For example, the seal may be provided by bonding the gap with a material, such as polyethylene (PE), polypropylene (PP), silicone, sealant, or a rubber, or applying the material to the gap.

According to an implementation, a component (e.g. a gasket) having a predetermined shape may be fabricated to provide the seal.

The barrier 140 may be provided as one or more rows, one or more columns, or a combination of rows and columns in the sample holder assembly 100, depending on the disposition of the heat sinks 130 and 131. The barrier 140 forming one row or column may be a connected structure of a plurality of barriers 140 or a single barrier 140 fabricated integrally.

FIGS. 2 to 4 illustrate the barrier 140 used in the heat sink 130.

In an implementation in which the plurality of sample holders 110 and 111 are used, the barrier 140 may be located between the adjacent heat sinks 130 and 131 thermally coupled different sample holders 110 and 111.

In an implementation in which the plurality of sample holders 110 and 111 are used, the barrier 140 may be located between the adjacent heat sinks 130 and 131 disposed on different sample holders 110 and 111.

The expression "heat sinks disposed on different sample holders" used in relation to the sample holders and the heat sinks may be used to refer to the heat sinks 130 used to cool the first sample holder 110 from among the plurality of sample holders 110 and 111 and the heat sinks 131 used to cool the second sample holder 111 other than the first sample holder 110. Although the sample holder 110 is not in direct contact with the heat sinks 130, the relative positions thereof may be represented.

In an implementation, the barrier 140 is not located between the adjacent heat sinks 131 and 133 thermally coupled to a single sample holder 111.

According to an implementation of the present disclosure, the barrier 140 is not located between the adjacent heat sinks 131 and 133 disposed on a single sample holder 111.

The expression "heat sinks disposed on a single sample holder" used in relation to the sample holders and the heat sinks may be used to refer to one or more heat sinks 131 and 133 used to cool the first sample holder 111 from among the plurality of sample holders 110 and 111.

The plurality of heat sinks 131 and 133 may be disposed separately on the sample holder 111, depending on the size (e.g. 16 wells, 24 wells, 32 wells, 60 wells, 90 wells, and 96 wells). In this case, the adjacent heat sinks 131 and 133 may be present on a single sample holder 111. In addition, the heat sinks 130 and 131 present on the adjacent sample holders 110 and 111 may be adjacent to each other.

The use of the barrier 140 may be adjusted depending on whether the adjacent heat sinks are disposed on different sample holders or on a single sample holder. For example, in FIG. 4, two heat sinks 130 and 132 and two heat sinks 131 and 133 are located below the sample holder 110 and the sample holder 111, respectively. In this case, the barrier 140 may be disposed between the adjacent heat sinks disposed on different sample holders, i.e. between the heat sink 130 and the heat sink 131 and between the heat sink 132 (not shown in FIG. 4) and the heat sink 133.

Since the barrier 140 is disposed between the heat sinks 130 and 131 disposed on different sample holders 110 and 111, independent temperature control of the different sample holders 110 and 111 may be more accurately realized.

In addition, the barrier 140 may not be located between the adjacent heat sinks disposed on the single sample holder, i.e. between the heat sink 130 and the heat sink 132 and between the heat sink 131 and the heat sink 133. Since the adjacent heat sinks disposed on the single sample holder participates in temperature control of the single sample holder, the barrier 140 may be selectively used.

In FIG. 4, the barrier 140 located between the heat sink 130 and the heat sink 131 and between the heat sink 132 and the heat sink 133 may be a single barrier or a connection of two barriers.

The barrier 140 according to an implementation of the present disclosure is located between all of the adjacent heat sinks.

Figure 5:
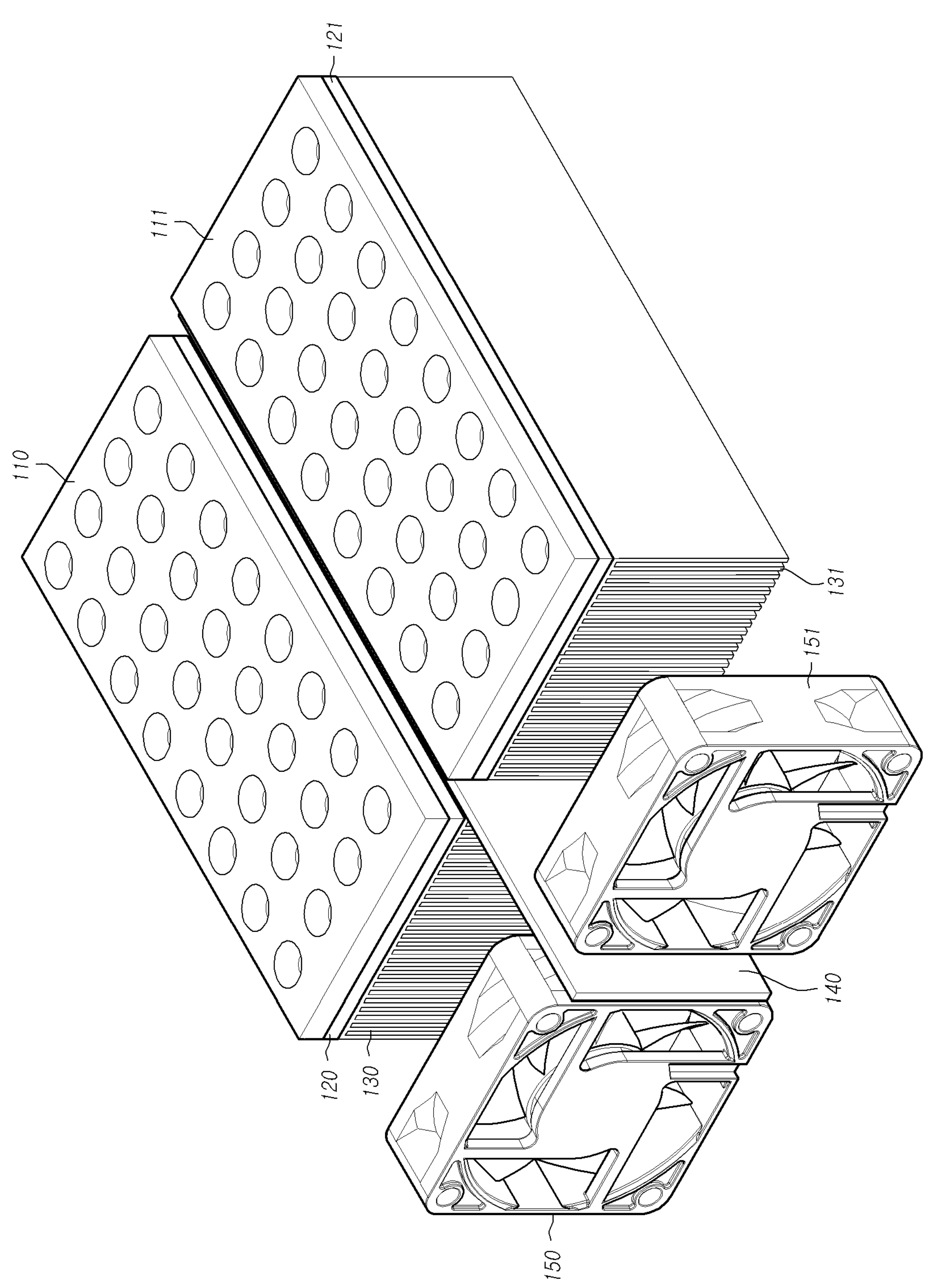
FIG. 5 is a perspective view illustrating another sample holder assembly according to embodiments of the present disclosure.

As illustrated in FIG. 5, in a case in which the two cooling fans 150 and 151 are adjacent to each other, the functions of the heat sinks 130 and 131 corresponding thereto may be affected. For example, in a case in which the cooling fan 150 supplies wind to the first heat sink 130 corresponding thereto, the wind of the cooling fan 150 may flow to the second heat sink 131 adjacent to the first heat sink 130. When the second cooling fan 151 is in the off state, an unexpected airflow may be provided to the second heat sink 131.

This phenomenon may affect the heat dissipation performance of the heat sinks 130 and 131, thereby causing a situation in which the temperatures of the sample holders 110 and 111 are not accurately controlled.

The barrier 140 may be used as in the heat sink 130 in order to prevent the thermal interference between the adjacent cooling fans 150 and 151.

In FIG. 1B, the barrier 140 is located between airflow paths of the adjacent cooling fans 150 and 151 to prevent the interference of the cooling fans 150 and 151 to the corresponding heat sinks 130 and 131.

FIG. 1C illustrates an example in which the barrier 140 is present not only between the adjacent heat sinks 130 and 131 but also between the adjacent cooling fans 150 and 151.

In a case in which it is necessary to distinguish the barrier 140 for the heat sink 130 and the barrier 140 for the cooling fan 150, the barrier 140 for the heat sink may be referred to as a "barrier 141," and the barrier 140 for the cooling fan may be referred to as a "barrier 142" (see FIG. 1C).

The foregoing description regarding the barrier 140 used between the heat sinks 130 may be applied in the same manner to the barrier 140 for the cooling fan 150. For example, the barriers may be fabricated from the same material and in the same shape, and may be provided in the same arrangement.

In an implementation, the sample holder assembly 100 includes the barrier 140 dividing airflow paths of one or more adjacent cooling fans 150 and 151 from among the cooling fans 150.

In an implementation, the expression "airflow path of the cooling fan 150" refers to the path from the cooling fan to the heat sink to be cooled by the cooling fan.

The expression "barrier 140 located between the adjacent cooling fans 150 and 151" refers to "the barrier 140 dividing the airflow paths of the adjacent cooling fans 150 and 151" unless otherwise specified.

The expression "barrier 140 dividing the airflow paths of the adjacent cooling fans 150 and 151" is used to include not only the barrier 140 extending to portions in which the adjacent cooling fans 150 and 151 are located but also the barrier disposed only in the airflow paths of the adjacent cooling fans 150 and 151.

As illustrated in FIGS. 1C, 4, and 5, in an implementation in which the plurality of sample holders 110 and 111 are used, the barrier 140 may be located between the airflow paths of the adjacent cooling fans 150 and 151 disposed on different sample holders 110 and 111.

The expression "cooling fans disposed on different sample holders" used in relation to the sample holders and the cooling fans may be used to refer to the cooling fans 150 located in positions in which the heat sink 130 used for the first sample holder 110 from among the plurality of sample holders 110 and 111 may be cooled and the cooling fans 151 located in positions in which the heat sink 131 used for the second sample holder 111 other than the first sample holder 110 may be cooled. Although the sample holder 110 and the cooling fan 130 are not disposed to be in direct contact with each other, the relative positions thereof may be indicated.

As illustrated in FIG. 4, in an implementation, the barrier 140 is not located between the airflow paths of the adjacent cooling fans 151 and 153 disposed on a single sample holder 111.

The expression "cooling fans disposed on a single sample holder" used in relation to the sample holder 110 and the cooling fan 150 may be used to refer to one or more cooling fans 150 located in portions in which the first sample holder heat sink 150 from among the plurality of sample holders 110 and 111 may be cooled.

The plurality of cooling fans 151 and 153 may be disposed separately on the sample holder 111, depending on the size (e.g. 16 wells, 24 wells, 32 wells, 60 wells, 90 wells, and 96 wells). In this case, the adjacent cooling fans 151 and 153 may be present on a single sample holder 111. In addition, the cooling fans 150 and 151 present on the adjacent sample holders 110 and 111 may be adjacent to each other.

The use of the barrier 140 may be adjusted depending on whether the adjacent cooling fans are disposed on different sample holders 110 and 111 or on a single sample holder 111.

According to an implementation of the present disclosure, the barrier 140 is located between the airflow paths of all adjacent cooling fans.

A variety of combinations of the components in the sample holder assembly 100 may be blocked by the barrier 140.

In an implementation, as illustrated in FIG. 1A, the barrier 140 may be disposed between the adjacent heat sinks 130 and 131.

In another implementation, as illustrated in FIG. 1B, the barrier 140 may be disposed between the adjacent cooling fans 150 and 151.

In another implementation, as illustrated in FIGS. 1C, 4, and 5, the barrier 140 may extend from between the heat sinks 130 and 131 to between the cooling fans 150 and 151.

In another implementation, the barrier 140 may extend from between the adjacent sample holders 110 and 111 to between the adjacent cooling fans 150 and 151 or extend from between the adjacent heat-generating elements 120 and 121 to between the adjacent cooling fans 150 and 151.

In the thermal cycler according to the present disclosure, a sealing material or component or a barrier component (such as a gasket) separate from the barrier 140 may be used to block between the sample holders 110 and 111 and/or between the heat-generating elements 120 and 121.

The sample holder assembly 100 including the sample holders 110 and 111, the heat-generating elements 120 and 121, the heat sinks 130 and 131, the cooling fans 150 and 151, and the barrier 140, illustrated in FIGS. 1A to 5, is located in the predetermined space within the thermal cycler.

In an implementation, the sample holder assembly 100 is accommodated in a sample holder assembly housing (not shown) located in a predetermined space within the thermal cycler.

In an implementation, the barrier 140 may be fixedly coupled to a specific component in the sample holder assembly 100, or may be fixed in the sample holder assembly housing.

In the sample holder according to the present embodiment, at least one heat-generating element and at least one cooling fan thermally coupled to the at least one heat-generating element and located below or on a side of the heat sink to dissipate heat from the heat sink are required. In addition, according to the present embodiment, the barrier 140 is located between the heat sinks 30 and 31.

The above-described components are intended to provide the independency of thermal control of the individual sample holders for amplification reactions in the sample holder assembly 100 of the thermal cycler according to the present disclosure.

In the drawings, two sample holders 110 and 111, two heat-generating elements 120 and 121, two heat sinks 130 and 131, and two cooling fans 150 and 151, as well as the barrier 140 located therebetween, are illustrated for the sake of brevity.

The sample holder assembly 100 may be provided with three or more constructions respectively including the sample holder 110, the heat-generating element 120 thermally coupled to the sample holder 110, the sample holder 110, the heat sink 130 thermally coupled to the heat-generating element, the cooling fan 150 disposed to cool the heat sink. In particular, the barrier may be present between the heat sinks and/or between the cooling fans of the adjacent sample holders.

In an implementation, the constructions may be 3, 4, 5, 6, 7, 8, 9, 10, 11, or 12 configurations.

The thermal cycler includes the controller to control the heat-generating element 120 and the cooling fan 150. One or more controllers may be used. For example, the heat-generating element 120 and the cooling fan 150 are controlled by a single controller. Alternatively, a controller for the heat-generating element 120 and a controller for the cooling fan 150 may be used. A controller may be used for each of the plurality of heat-generating elements 120 and the plurality of cooling fans 150. In a case in which a plurality of controllers are used, a controller for integrally controlling these controllers may be used.

The sample holder assembly 100 according to the present disclosure further includes a sample holder accommodating unit 160.

In a case in which the sample holder 110 is the thermal block, the sample holder accommodating unit 160 for accommodating the sample holder 110 is additionally included. In the present disclosure, the barrier 140 may be connected to the sample holder accommodating unit 160. In particular, the barrier 140 may be located below the sample holder accommodating unit 160.

Figure 6:
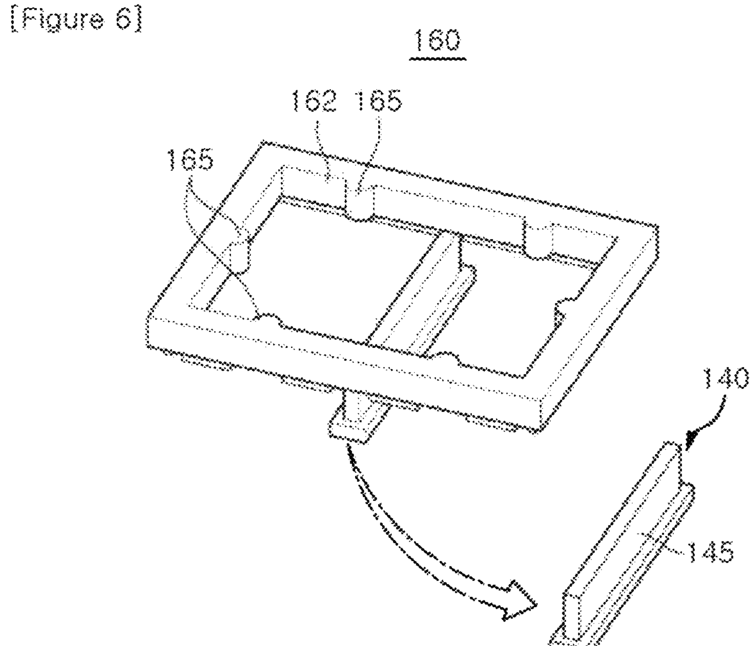
FIG. 6 is a top perspective view illustrating the sample holder assembly according to embodiments of the present disclosure, in which the sample holder accommodating unit and the barrier are provided.

FIG. 6 is a top perspective view illustrating the sample holder accommodating unit 160 and the barrier 140 according to embodiments of the present disclosure.

Figure 7:
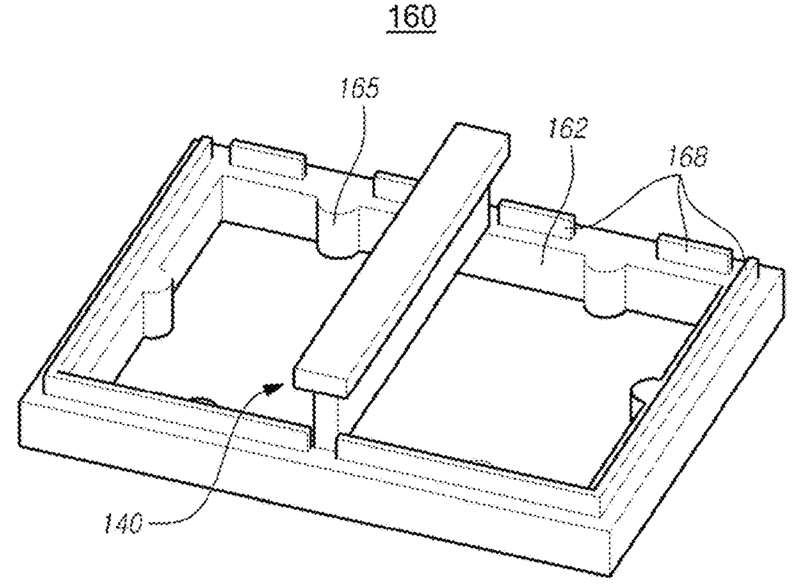
FIG. 7 is a bottom perspective view illustrating the sample holder assembly according to embodiments of the present disclosure, in which the sample holder accommodating unit and the barrier are provided.

FIG. 7 is a bottom perspective view illustrating the sample holder accommodating unit 160 and the barrier 140 according to embodiments of the present disclosure.

The sample holder accommodating unit 160 is configured to be a frame open through the top and bottom portions thereof.

The sample holder accommodating unit 160 having the open structure includes a receiving portion 162 capable of accommodating a plurality of sample holders (or thermal blocks). The receiving portion 162 may accommodate the plurality of sample holders.

According to an implementation, in the receiving portion 162, each of the plurality of sample holders maintains predetermined distances from the adjacent sample holders. Here, hollow spaces are defined between the sample holders. Alternatively, screens by which the receiving portion 162 may be divided according to the sample holders may be included in place of the hollow spaces. The screens may be disposed between the sample holders and connected to the barrier 140 located therebelow. The screens may be made of a heat insulating material to provide thermal independence between the sample holders.

In an implementation, the sample holder accommodating unit 160 refers to a structure or a housing accommodating the sample holders.

In an implementation, the structure or housing of the sample holder accommodating unit 160 is generally, a square shape but may have different shapes.

In an implementation, the sample holder accommodating unit 160 has the shape of a quadrangular frame. Due to the structure having the open top and bottom portions, the receiving portion 162 is provided, and the sample holder is accommodated.

According to an implementation of the present disclosure, the receiving portion 162 of the sample holder accommodating unit 160 includes clamping portions 165. The clamping portions 165 fix the sample holder by compressing the sample holder in the top to bottom direction (or the inward direction).

The clamping portions 165 may maintain the sample holders introduced into the receiving portion 162 in horizontal positions, so that each of the sample holders is not dislodged upwards.

In addition, the clamping portions 165 fix the sample holders by pressing the sample holders in the top to bottom direction, thereby preventing the sample holders from bouncing from the receiving portion 162.

In an implementation, two or more clamping portions 165 may be provided on the inner surfaces of the receiving portion 162 to clamp the corresponding sample holder. To increase clamping force, the clamping portions 165 according to the present embodiment may be provided on inner surfaces between the wells located on the side surfaces of the sample holders, and may have the shape of fitting protrusions depending on the shape of the sample holders. Due to the fitting protrusions, the sample holders may be engaged and disengaged.

According to an implementation of the present disclosure, in a case in which the receiving portion 162 is provided with the partitioning screens according to the sample holders, one or more clamping portions 165 may be provided on each of the screens, so that strong fixing force may be obtained.

According to an implementation of the present disclosure, as illustrated in FIG. 7, the sample holder accommodating unit 160 includes insertion portions 168. The insertion portions 168 allow the heat-generating elements 120 and 121, the heat sinks 130 and 131, and the receiving portion 162 coupled to the insertion portions 168 to be reliably connected to each other, so that the components are firmly coupled to each other.

In the process in which the heat-generating element 120 and the heat sink 130 coupled to the sample holder are connected to the sample holder accommodating unit 160, the outer side surfaces of the heat-generating element 120 and the heat sink 130 may be in close contact with the insertion portions 168. Thus, connection fitting is convenient, and the heat-generating element 120 and the heat sink 130 coupled to the sample holder may be prevented from being offset to one side.

To fix the sample holder accommodated in the sample holder accommodating unit 160 or fill the gap between the sample holder accommodating unit and the sample holder, a seal may be provided on a side surface of the sample holder, more particularly, between a side surface of the bottom portion and the sample holder accommodating unit 160.

The seal may be implemented by a variety of methods, for example, by bonding the gap with polyethylene (PE), polypropylene (PP), silicone, sealant, or a rubber, or applying the material to the gap, so that adhesive is improved and wind and heat resistance functions are significantly improved.

Figure 8:
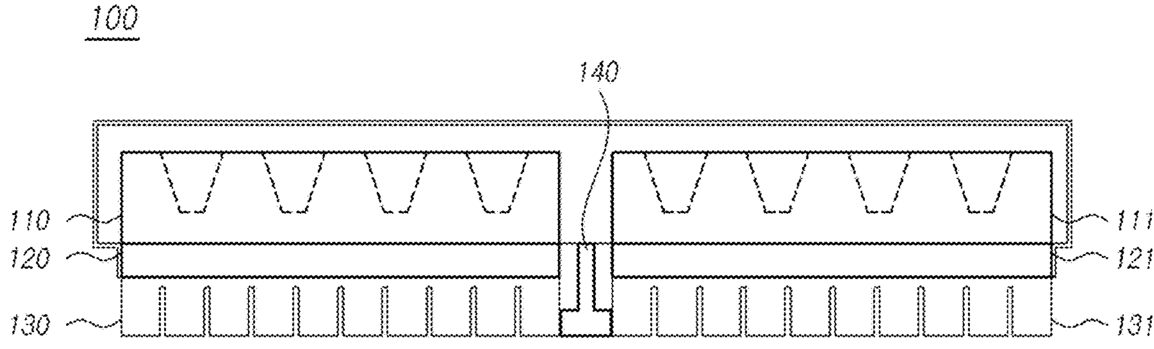
FIG. 8 is a side view illustrating the sample holder assembly according to embodiments of the present disclosure, in which the sample holder accommodating unit is provided.

FIG. 8 is a side view illustrating the sample holder assembly 100 including the sample holder accommodating unit 160. In the receiving portion 162 of the sample holder accommodating unit 160 serving as the thermal block accommodating unit, two sample holders 110 and 111 serving as thermal blocks are located, the heat-generating elements 120 and 121 are located below the sample holders 110 and 111 serving as the thermal blocks, the heat sinks 130 and 131 are located below the heat-generating elements 120 and 121, the cooling fans 150 are located below heat-generating elements 120 and 121, the barrier 140 is located between the adjacent heat sinks 130 and 131 and connected to the sample holder accommodating unit 160.

In the present disclosure, the barrier 140 may be connected to the sample holder accommodating unit 160. In particular, the barrier 140 may be located below the sample holder accommodating unit 160.

As the receiving portion 162 accommodates the plurality of sample holder sample holders 110 and 111, the heat-generating elements 120 and 121 and the heat sinks 130 and 131 thermally coupled to the sample holders 110 and 111 serving as the thermal blocks may also be present.

In a case in which the heat sinks are adjacent to each other, airflows of the heat sinks overlap and collide with each other on portions of the heat sinks facing each other. Consequently, such airflows may be dispersed inwardly instead of being discharged outwardly, thereby affecting the heat dissipation function of the adjacent heat sinks.

To prevent this problem, the barrier 140 may be connected to the bottom portion of the sample holder accommodating unit 160 according to the present disclosure.

The barrier 140 may be provided integrally on the sample holder accommodating unit 160 or may be detachably coupled to the sample holder accommodating unit 160. The barrier 140 according to an embodiment of the present disclosure may be detachably coupled to the bottom portion of the sample holder accommodating unit 160 as required via a separate means. A component participating in the detachable attachment of the barrier 140 may be provided on the bottom portion of the sample holder accommodating unit 160.

For example, the sample holder accommodating unit 160 and the barrier 140 may have a variety of shapes. For example, the sample holder accommodating unit 160 and the barrier 140 may be provided as a recess and a protrusion coupled to each other by fitting, or may be attached to each other by bonding.

According to an implementation of the present disclosure, the barrier 140 may be provided in a housing in which the sample holder accommodating unit 160 is accommodated. For example, the barrier 140 may be connected to a wall surface of the housing in which sample holder accommodating unit 160 is accommodated.

According to an implementation of the present disclosure, the barrier 140 located on the bottom portion of the sample holder accommodating unit 160 further includes a clamping portion 145 by which the barrier 140 may be bound to a portion of the heat sink 130.

The clamping portion 145 of the barrier 140 may be located on the bottom end portion of the barrier 140, such that both side surfaces of the clamping portion 145 may protrude beyond the top surface of the barrier 140 in the lateral direction. Due to the bottom end portion protruding by the distance between the barrier 140 and the heat sink 130, the clamping portion 145 of the barrier 140 may be bound to one surface of the heat sink 130 to support weight added to the heat sink 130 from the sample holder and the heat-generating element 120 located below the sample holder.

FIG. 9 is a perspective view illustrating the sample holder accommodating unit 160 according to an implementation of the present disclosure in which three sample holders are accommodated. In the receiving portion 162 of the sample holder accommodating unit 160, the screens 166 capable to partitioning the sample holders may be present between the entire sample holders or selected sample holders.

It will be understood that the terms "comprise", "include", "have", and any variations thereof used herein are intended to cover non-exclusive inclusions unless explicitly described to the contrary. Unless otherwise specified, all terms including technical and scientific terms used herein have the same meaning as that commonly understood by those having ordinary knowledge in the technical field to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The above description and the accompanying drawings provide an example of the technical idea of the present disclosure for illustrative purposes only. Those having ordinary knowledge in the technical field, to which the present disclosure pertains, will appreciate that various modifications and changes in form, such as combination, separation, substitution, and change of a configuration, are possible without departing from the essential features of the present disclosure. Therefore, the embodiments disclosed in the present disclosure are intended to illustrate the scope of the technical idea of the present disclosure, and the scope of the present disclosure is not limited by the embodiment. The scope of the present disclosure shall be construed on the basis of the accompanying claims in such a manner that all of the technical ideas included within the scope equivalent to the claims belong to the present disclosure.

The foregoing detailed descriptions of specific exemplary embodiments of the present disclosure have been and are not intended to be exhaustive or to limit the present disclosure to the precise forms disclosed, and obviously a number of modifications and variations are possible for those having ordinary knowledge in the art in light of the above teachings. It is intended therefore that the scope of the present disclosure not be limited to the foregoing embodiments, but be defined by the Claims appended hereto and their equivalents.

The invention claimed is:

1. A thermal cycler comprising a sample holder assembly, wherein the sample holder assembly comprises:

a plurality of sample holders, wherein each of the plurality of sample holders has a hole configured to receive a sample reaction vessel, and wherein a temperature of each of the plurality of sample holders is configured to be independently controlled by a controller;

a plurality of peltiers, wherein at least one peltier of the plurality of peltiers is thermally coupled to a bottom surface of each of the plurality of sample holders;

a plurality of heat sinks, wherein at least one heat sink of the plurality of heat sinks is thermally coupled to a bottom surface of each of the plurality of peltiers;

a plurality of cooling fans configured to supply airflow toward the plurality of heat sinks, wherein the plurality of cooling fans are disposed below or adjacent to the plurality of heat sinks;

a sample holder accommodating unit including a receiving portion defined by a frame structure open at a top and a bottom, the plurality of sample holders being received in the receiving portion; wherein the receiving portion includes a screen interposed between adjacent ones of the plurality of sample holders, the screen separating the adjacent sample holders, wherein the screen is a thermal insulator; and a solid barrier connected to the screen and located below the screen, wherein the solid barrier is a thermal insulator positioned between adjacent heat sinks of the plurality of heat sinks, and wherein the adjacent heat sinks are thermally coupled to different sample holders among the plurality of sample holders.

2. The thermal cycler according to claim 1, wherein the solid barrier is further located in a region between airflow passages defined by adjacent cooling fans of the plurality of cooling fans, and wherein the adjacent cooling fans are thermally coupled to different sample holders among the plurality of sample holders.

3. The thermal cycler according to claim 1, wherein each of the plurality of sample holders is thermally coupled to two or more heat sinks of the plurality of heat sinks.

4. The thermal cycler according to claim 1, wherein each of the plurality of sample holders is configured to be cooled by two or more cooling fans of the plurality of cooling fans.

* * * * *